United States Patent
Brand et al.

(10) Patent No.: US 6,614,038 B1
(45) Date of Patent: Sep. 2, 2003

(54) METHOD FOR MONITORING THE IRRADIATION CONTROL UNIT OF AN ION-BEAM THERAPY SYSTEM

(75) Inventors: Holger Brand, Darmstadt (DE); Thomas Haberer, Darmstadt (DE); Klaus Poppensieker, Darmstadt (DE); Dieter Schardt, Darmstadt (DE); Bernd Voss, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/913,741

(22) PCT Filed: Feb. 3, 2000

(86) PCT No.: PCT/EP00/00859

§ 371 (c)(1),
(2), (4) Date: Dec. 5, 2001

(87) PCT Pub. No.: WO00/48678

PCT Pub. Date: Aug. 24, 2000

(30) Foreign Application Priority Data

Feb. 19, 1999 (DE) .......................................... 199 07 771

(51) Int. Cl.[7] ................................................ A61N 5/10
(52) U.S. Cl. ............................... 250/492.3; 250/505.1; 250/398; 250/496.1; 250/396 HL; 328/235; 328/233; 328/234
(58) Field of Search .............................. 250/492.3, 398, 250/496.1, 396 HL, 306, 307, 251; 328/235, 233, 234

(56) References Cited

U.S. PATENT DOCUMENTS 4,870,287 A 9/1989 Cole et al.
5,117,829 A 6/1992 Miller et al.
5,585,642 A 12/1996 Britton et al.

FOREIGN PATENT DOCUMENTS

EP 0 986 070 A1 * 3/2000 ............ G21K/5/10

OTHER PUBLICATIONS

E. Pedroni, "Beam Delivery",*Hadrontherapy in Oncology*, Elsevier Science B.V. 1994, pp. 434–452.

H.F. Weehuizen, P.M. Cronje, R.K. Fisch, P.J. Theron, H. Kettner; "Closed Loop Control of a Cyclotron Beam for Proton Therapy", *National Accelerator Cetre, KEK Proceedings 97–17*, 1998.

G. Kraft, U. Arndt, W. Becher, D. Schardt, H. Stelzer, U. Weber, Th. Archinal, "Heavy Ion Therapy at GSI", *Nuclear Instruments & Methods in Physics Research* A 367, 1995, pp. 66–70.

* cited by examiner

*Primary Examiner*—John R. Lee
*Assistant Examiner*—Zia R. Hashmi
(74) *Attorney, Agent, or Firm*—Frommer Lawrence & Haug, LLP; Ronald R. Santucci (57) ABSTRACT

The invention relates to a method of checking the calculated [sic] irradiation control unit of an ion beam therapy system which comprises a raster scanning device arranged in a beam guidance system and having vertical deflection means and horizontal deflection means for the vertical and horizontal deflection of a treatment beam at right angles to its beam direction, so that the treatment beam is deflected by the raster scanning device onto an isocenter of the irradiation station and scans a specific area surrounding the isocenter, data sets and permanently stored data of a control computer, parameters of measuring sensors and desired current values of scanner magnets being checked.

23 Claims, 2 Drawing Sheets

METHOD FOR MONITORING THE IRRADIATION CONTROL UNIT OF AN ION-BEAM THERAPY SYSTEM

The present invention relates to a method of checking the irradiation control unit of an ion beam therapy system which, in particular, is operated with heavy ions.

Ion beam therapy systems are preferably used for the treatment of tumors. They have the advantage that when a target is irradiated, the major part of the energy of the ion beam is transferred to the target, while only a small amount of energy is transmitted to sound tissue. Therefore, a relatively high irradiation dose can be used to treat a patient. By contrast, X-rays transmit their energy to the same extent to the target and to sound tissue, so that, for health reasons in order to protect the patient, a high irradiation dose cannot be used.

U.S. Pat. No. 4,870,287, for example, discloses an ion beam therapy system in which proton beams are generated by a proton source, it being possible for its protons to be fed to various treatment or irradiation stations via an accelerator device. At each treatment station there is a rotating frame with a patient couch, so that the patient can be irradiated with the proton beam at different irradiation angles. While the patient is located physically at a fixed point within the rotating frame, the rotating frame rotates about the body of the patient in order to focus the irradiation beams at different irradiation angles onto the target, located at the isocenter of the rotating frame. The accelerator device comprises the combination of a linear accelerator (LINAC) and a synchrotron ring, as it is known.

In H. F. Weehuizen et al, CLOSED LOOP CONTROL OF A CYCLOTRON BEAM FOR PROTON THERAPY, KEK Proceedings 97-17, January 1998, a method of stabilizing the proton beam in proton beam therapy systems is proposed, the treatment beam being controlled actively in such a way that, at two measurement points spaced apart from each other in the longitudinal direction, it lies on the center line of the corresponding beam feed system. The first measurement point is located between a pair of deflection magnets and is formed by a multiwire ionization chamber. Depending on the current value, supplied by this multiwire ionization chamber, of the beam position with respect to the center of the beam path, the PI control of further deflection magnets, which are arranged upstream of the first-named pair of deflection magnets, is produced. The second measurement point is located shortly upstream of the isocenter and is formed by an ionization chamber subdivided into four quadrants. Depending on the current position value from this ionization chamber, again PI control signals are generated, but these are intended for the first-named deflection magnets. The intention of this control is to permit both angular stability with respect to the center line of the beam feed system and lateral positional stability of the proton beam.

When carrying out heavy ion irradiation, that is to say an irradiation using ions which are heavier than protons, large and heavy equipment is required, however, so that here there is the tendency to avoid the use of rotary frameworks and, instead, to move the patient or the patient couch. Corresponding therapy systems are described, for example, in E. Pedroni: Beam Delivery, Proc. 1st Int. Symposium on Hadrontherapy, Como, Italy, Oct. 18–21, 1993, page 434. These systems are accordingly eccentric systems.

Since, however, fundamentally isocentric systems are preferred by oncologists, a heavy ion beam therapy system has been proposed in which, although rotary frameworks are used at the treatment stations, the radii of the rotary frameworks can be reduced by the treatment beam fed to each rotary framework horizontally along its axis of rotation being guided, with the aid of suitable magnetic and optical arrangements, in such a way that it firstly runs away from the axis of rotation and subsequently crosses the axis of rotation again at the isocenter in order to irradiate a target. In order to irradiate the target, a raster scanner is provided, which comprises vertical deflection means and horizontal deflection means which each deflect the treatment beams at right angles to the beam axis, so that an area surrounding the target is scanned by the treatment beams. This system therefore substantially provides beam guidance in only one plane of the rotary framework.

The irradiation by means of the raster scanner is carried out with the aid of irradiation dose data, which are calculated by the control system of the ion beam therapy system automatically, depending on the patient to be irradiated or to be treated.

Since, in principle, high operational safety and operational stability with regard to the treatment beam are required of ion beam therapy systems, in the case of the heavy ion beam therapy system described previously, a monitoring device is provided to monitor the treatment beam supplied by the raster scanner. This monitoring device is arranged between the last deflection magnet of the aforementioned magnet arrangement and the isocenter, and may comprise ionization chambers for monitoring the particle flux and multiwire chambers for monitoring the beam position and the beam width.

During the operation of medical electron accelerators, various DIN standards have to be complied with for reasons of safety. These relate firstly to acceptance testing, that is to say checking the operational readiness, and secondly testing the constancy, that is to say checking the operational stability, of the system. For ion beam therapy systems, in particular for heavy ion beam therapy systems, such safety standards developed specifically for ion beam therapy systems are not yet known. However, in the case of ion beam therapy systems there is also the requirement for the greatest possible operational safety and operational stability.

The present invention is therefore based on the object of proposing a method of checking the irradiation control unit of an ion beam therapy system, in order to improve the operational safety and operational stability, in particular as referred to checking the irradiation control unit. At the same time, the intention is for the method to be suitable in particular for use with heavy ions.

According to the present invention, this object is achieved by a method having the features of claim 1. The dependent claims in each case define preferred and advantageous embodiments of the present invention.

According to the present invention, an ion beam therapy system is operated which comprises a raster scanner device arranged in a beam guidance system and having vertical deflection means and horizontal deflection means for the vertical and horizontal deflection of a treatment beam at right angles to its beam direction, so that the treatment beam is deflected by the raster scanner device onto an isocenter of the irradiation station and scans a specific area surrounding the isocenter, data sets and permanently stored data of a control computer, parameters of measuring sensors and desired current values of scanner magnets being checked. To this end, the data sets and programs to be loaded into front end processors from the central control computer are read back after being loaded and compared with the output data. The permanent storage of permanently stored data is checked. Desired current values of scanner magnet currents are compared with actual magnet current values. Calibration tests of measuring sensors are carried out.

The electrical charge produced in the ionization chambers of the monitoring system of the therapy system, said charge being used to determine the number of particles, depends on the pressure and the temperature of the ionization chamber gas, so that these two variables must be monitored and logged during the irradiation. The pressure and the temperature of the gas of the ionization chambers are measured with the aid of electrical sensors, the measured values being recorded about once per minute by the monitoring system, being converted into absolute units (hPa and ° C.) with input calibration factors and displayed digitally. The time variation of the measured values can be displayed graphically in a trend graph. The sensors are calibrated with the aid of reference measuring instruments. The calibration of the sensors fitted in the ionization chambers should be repeated before each therapy irradiation block. In addition, the air pressure and the room temperature at the location of the monitoring system are measured with absolutely calibrated instruments and registered by the monitoring system and also logged during each irradiation. Thus, for the (daily) checking of the ionziation chambers, the absolute values for air pressure and room temperature can be read off directly on the reference measuring instruments, compared with the values displayed by the monitoring system and logged. In this case, the reference values used are the measured values registered during the daily calibration of the monitoring system. In the event of a deviation of 28 hPa or 5° C., respectively, an alarm is triggered by the monitoring system.

In addition, the loading of programs and data sets into the control computer of the ion beam therapy system must be checked. This is necessary in order to be able to load data which are required for a patient irradiation correctly into the sequence control of the system. Only if all the data are correct may a patient irradiation be started. For this purpose, with the aid of specific programs in the server computers of the monitoring system, programs and data are written into the individual processors of the control computers, are read back and compared with the programs and data stored in the dedicated memories, these test programs being executed automatically before each irradiation. Only if the data loaded back correspond exactly to the data stored in the data memories of the monitoring system can safe operation be assumed. In the event of deviations, an alarm message is generated, and the interlock unit previously described, which is used to prevent irradiation, cannot be released.

A further testing aspect relates to the switching of the currents for the deflection magnets of the raster scanner. In this case, it is necessary to ensure that the current values of these deflection magnets reach a determined desired value, set in the magnetic network devices, both in terms of value and also in terms of time within specific tolerance limits. For this purpose, the time between the setting of a magnet current value in the magnetic network devices and the reaching of the corresponding stable magnet current is measured for various current values. The maximum tolerable current accuracy with respect to a deviation from the set magnet current value is 0.3 A. The maximum tolerable setting time in the event of a current step of 2 A is 175 $\mu$s in the x direction and 325 $\mu$s in the y direction. If these tolerances are not complied with, the irradiation must be shut down. In order to check consistency, this test can be carried out before each irradiation block.

Finally, it is also necessary to ensure that the number of the irradiation point that is active when a shutdown condition occurs is stored permanently, that is to say secured against power failure. This permits the continuation of the irradiation, approved by authorized persons, at a later time. The serviceability of this implemented safety function can be checked by a specific irradiation or treatment plan being loaded into the monitoring system and executed without any irradiation, that is to say simulated. In the case of a specific irradiation site, the power supply of the sequence controller is switched off and, after the system has been restarted, the last irradiation site is read out and compared with the irradiation site when the power supply was switched off. If there is non-agreement, an appropriate intervention is made. To test consistency, this check is carried out before each irradiation block.

In particular, it is proposed to check the calculated irradiation dose values for a number of measurement points on the phantom, conclusions being drawn as to the adequate accuracy of the calculation of the irradiation dose data if the mean deviation between the calculated and measured values of the irradiation dose for all the measurement points does not exceed a predefined first tolerance value and, for each individual measurement point, the deviation between the calculated and measured irradiation dose for this measurement point does not exceed a predefined second tolerance. In this case, the first tolerance value is ±5% and the second tolerance value is ±7%.

In order to check the correct transmission of the geometric structures at the treatment station and the planning parameters of an image-providing device belonging to the ion beam therapy system as far as the positioning means, a digital reconstruction of the phantom, in particular a radiographic reconstruction, can be calculated and is compared with a radiograph of the phantom which is produced, in order to detect any possible deviation.

The present invention permits a considerable improvement in the operational stability and operational safety of the ion beam therapy system and defines a testing plan with specific testing aspects, which can be carried out with the effect of acceptance testing and/or consistency testing of the ion beam therapy system. This relates in particular to the irradiation planning, in the course of which irradiation dose data in the ion beam therapy system are calculated automatically, depending on the patient to be irradiated or treated.

The invention will be described below using a preferred exemplary embodiment and with reference to the appended drawing, in which.

An ion beam therapy system on which the present invention is based is generally used in hospital buildings, which are subdivided into a medical area and an accelerator area. In order to treat patients, a number of treatment or irradiation stations are provided. The control system of the ion beam therapy system comprises a number of control rooms, it being possible for technical control rooms to be provided for the individual treatment stations and a main control room for the accelerator device. Furthermore, laboratories for dosimetry or for accelerator maintenance or a PET device (Positron Emitter Tomograph) can be accommodated in the building. In addition, power supply equipment (especially for the accelerator device and the irradiation system) and cooling equipment are provided. The individual treatment rooms are bounded by thick walls and ceilings which, for example, consist of concrete with a thickness of 2 m, in order to ensure an adequate shielding effect.

Since the basic structure of the ion beam therapy system is substantially not the theme of the present invention, it will be discussed only briefly at this point.

Figure 1:
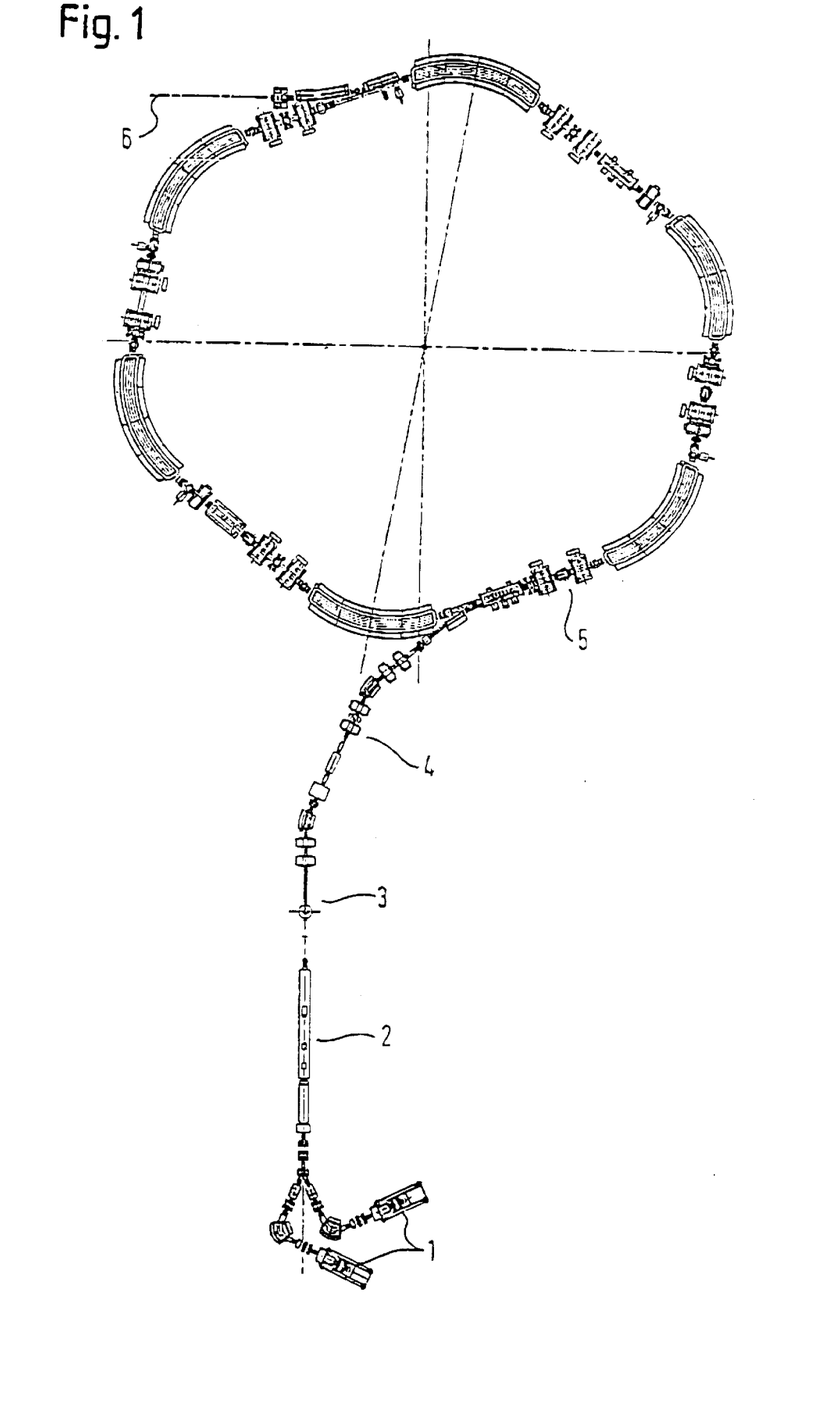
FIG. 1 is a simplified schematic illustration of an accelerator device used in the present ion beam therapy system.

The ion beam therapy system comprises an injection system which, together with the accelerator device already previously mentioned, is illustrated in simplified form in FIG. 1.

The injection system comprises ion sources 1, whose radiation is fed, in each case via low energy beam guidance lines having an arrangement of spectrometer magnets and quadrupoles, to a switching magnet, which feeds the radiation, inter alia via a further quadrupole arrangement and a chopper arrangement provided for pulse shaping, to a linear accelerator 2 (LINAC).

In the present exemplary embodiment, the intention is for only $^{12}C^{2+}$ ions to be used, which are stripped to $^{12}C^{6+}$ in the beam guidance between the linear accelerator 3 and the synchrotron ring 5. For this purpose, a stripper 3 is provided downstream of the linear accelerator 2. Because of their physical and biological characteristics, these carbon ions have been shown to be very effective in the treatment of tumors, and have the advantages of high physical selectivity and high biological effectiveness and, moreover, offer the possibility of verifying the irradiation with the aid of a positron emitter tomograph (PET). By means of the suitable selection of the carbon ions, the biological effectiveness can be controlled in such a way that it is low in the plateau region of the Bragg curve and is high in the region of the Bragg peak. As a result, the target or the tumor can be treated with a higher dose, while the dose for the surrounding healthy tissue is minimized.

In order to ensure the use or acceleration only of the intended sort of ions, a charge spectrum of the present beam is recorded in the high-charge injection system and is evaluated. By comparing the recorded charge spectrum with a reference spectrum, undesired ions or interferences can be detected and appropriate measures can be taken. This check can be carried out, for example, each time an ion source 1 is run up.

The linear accelerator 2 is used for the first acceleration of the ions fed to it, which are then fed via an injection line 4 to the synchrotron 5. The injection line 4 comprises, in addition to the stripper 3 already mentioned, a further chopper arrangement for the fine shaping of the injection pulses, dipole magnets for charge analysis, quadrupoles for adapting the radiation to the storage capacity of the synchrotron 5, etc.

The injection system, which inter alia comprises the ion sources 1, the low energy beam guidance lines, the linear accelerator 2 (LINAC), the stripper 3 and the injection line 4, therefore has overall the task of producing and analyzing ion beams with desired particles, monitoring the contamination of the ion beams and controlling the ion beam intensity, accelerating the ions to a specific injection energy and determining the pulse length of the pulses injected into the synchrotron ring 5.

The synchrotron ring 5 is used for the final acceleration of the ions fed to it to a specific energy and comprises, for example, a number of deflection magnets, quadrupoles and sextupoles. In the exemplary embodiment shown in FIG. 1, by way of example six deflection magnets with a deflection angle of 60° each are provided. Arranged inside the synchrotron 5 is a cooling device (not shown). By means of multiple injection circuits, the injected ions are accelerated from an energy in the region of a few MeV/u to an energy of, for example, over 400 MeV/u. The treatment beam accelerated in this way is extracted from the synchrotron at a specific point via a high energy beam guidance line 6 and supplied to the individual treatment stations.

Although the horizontal and vertical beam widening at the treatment station is generally different, the requirements for an "ideal" symmetrical and stable beam form at the treatment station can substantially be taken into account by means of suitable setting of the beam optics in the beam guidance lines.

The high energy beam guidance line 6 comprises quadrupole lenses, deflection magnets, beam analysis devices and so on. Furthermore, a further chopper can be arranged downstream of the extraction point from the synchrotron 5 and be used in emergency situations to interrupt the beam feed. In addition, provision can be made for a routine interruption of the extraction operation which is used to couple the treatment beam out of the synchrotron 5, after each raster scanning section.

Figure 2:
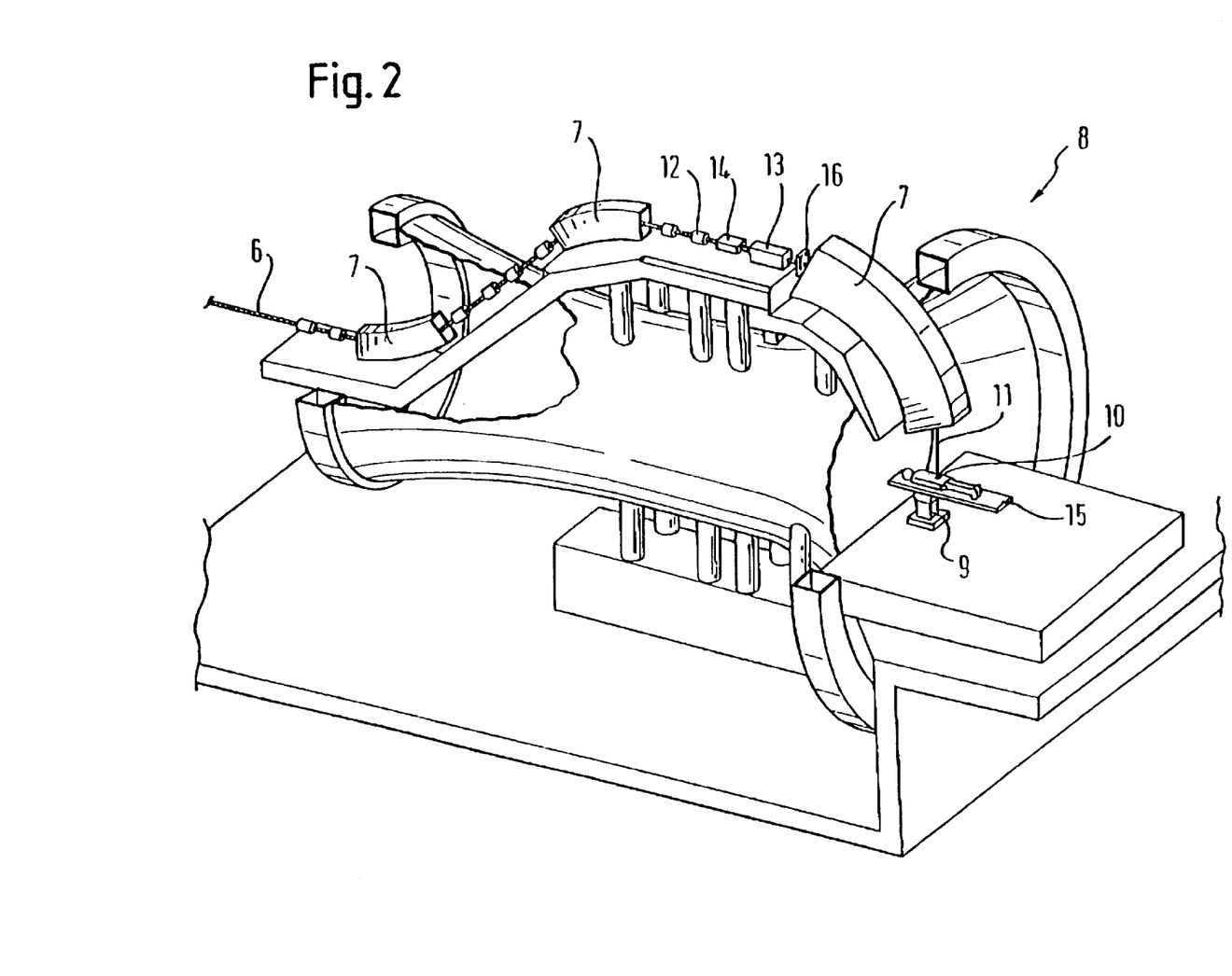
FIG. 2 shows a view of a rotary framework used in the present ion beam therapy system.

FIG. 2 shows a perspective view of one of the rotating frames 8 which are each provided at one of the treatment stations to which the treatment beam is fed via the above-described high energy beam guidance line 6. The rotating frame 8 rotates about a specific axis of rotation, while a patient to be treated is lying on a patient couch 9 in a locally fixed orientation or alignment. The part of the body of the patient which is to be treated is located at the isocenter 10 of the treatment beam, the isocenter being defined as the point of intersection between the central beam 11 of the raster scanner, described in more detail below, and an axis of rotation of the patient couch 9.

As can be seen from FIG. 2, the high energy beam guidance line 6 is configured in such a way that the treatment beam, after entering the rotating frame 8, is repeatedly deflected in one plane. For this purpose, a number of quadrupole lenses 12 and dipole magnets 7 are provided, the first two dipole magnets 7 having identical deflection angles, for example 42°, and being arranged opposite each other, while the last dipole magnet 7 is one deflection magnet with a deflection angle of 90°, so that the treatment beam 11, after entering the rotating frame 8, is first deflected laterally out of the axis of rotation of the rotating frame 8 and is then guided parallel to the axis of rotation of the rotating frame 8, in order then to emerge from the last deflection magnet 7, via a beam outlet opening, at an angle of 90° with respect to the patient couch 9.

The raster scanning arrangement provided in the case of the present ion beam therapy system is arranged between the last quadrupole lens 12 and the last deflection magnet 7 of the rotating frame 8 in the exemplary embodiment shown in FIG. 2, and comprises at least one horizontal raster scanner magnet 13 and at least on vertical raster scanner magnet 14. The raster scanner magnets 13 and 14 deflect the ion beam 11 in each case at right angles to the beam axis 11, either horizontally or vertically, so that the ion beam 11 rastered in this way, after emerging from the last deflection magnet 7, scans a specific area surrounding the isocenter 10 in agreement with a predefined treatment plan. Because of the arrangement of the raster scanner 13, 14 between the last quadrupole magnet 12 and the last deflection magnet 7, high flexibility can be achieved in the control, described in more detail below, of the beam size and beam dispersion at the isocenter 10.

The raster scanner magnets 13, 14 are driven by a control device (not illustrated), which is a constituent part of the overall control system of the ion beam therapy system.

Provided in the region between the beam outlet opening from the last deflection magnet 7 and the isocenter 10 are monitoring means for monitoring the treatment beam 11.

These monitoring means, which are provided for example to register and control the beam position, beam shape and the particle flux, will be explained more extensively below.

As has already been mentioned previously, in addition a positron emitter tomograph (PET) can be provided for monitoring the irradiation procedure, its image sensor (camera) being aligned in an in-beam position. The positron emitter tomography is preferably carried out during the treatment or irradiation. When a treatment beam strikes tissue, isotopes emitting positrons are generated, originating from the primary ions. Some of these isotopes, which differ from the primary ions merely by the loss of one or two neutrons, stop virtually in the same region as the corresponding primary ions. This stopping point of the positron emitters, as they are known, can be determined in order to monitor the irradiation procedure with the aid of positron emitter tomography.

For the ion beam therapy system previously described, a comprehensive testing system for checking and controlling the essential performance features of the therapy system has been developed, and will be discussed in more detail below.

A first section of the testing system relates to the production of the treatment beam 11.

In addition to the checking of the ion sort, already described previously, the beam energy of the treatment beam is also monitored. This is necessary because the beam energies required by the respective therapy have to be complied with. For this purpose, the monitoring means indicated in FIG. 2 comprise an absorber ionization chamber system, which has to be arranged at the isocenter 10 of the respective treatment station. The absorber ionization chamber system measures the position of the Bragg peak at the treatment station for a few selected energy levels which are activated during a therapy test cycle, the instantaneous beam energy being given by the measured position of the Bragg peak. In order to determine the position of the Bragg peak, the Bragg curves are measured in fine steps. If, during the check, a deviation of the Bragg peak from the desired position by more than 0.5 mm results, intervention is necessary. In order to test consistency, the testing procedure previously described can be carried out before each irradiation block.

A further minor point with regard to checking the treatment beam relates to monitoring the intensity level of the slowly extracted treatment beam at the irradiation or treatment station. The limited dynamics of the raster scanner limit the scanning speed of the rastered treatment beam upward, the component that is critical for this limitation being the maximum current slew rate of the magnetic power supply equipment. The scanning speed of the treatment beam depends on the respective intensity of the beam and the planned particle population. In order to ensure that the maximum scanning speed is not reached during irradiation, the particle rate extracted from the synchrotron 5 must not substantially exceed the preset desired value. If the value falls considerably below this, on the other hand, the overall irradiation time is prolonged, the control or monitoring system then possibly being operated in the region of very small input currents, which can result in impairment of the precision of the beam detection. Therefore, in the case of the present therapy system, measurement and logging of the particle intensities in the synchrotron in the upper intensity rate, and also of the particle rate fed to the irradiation station, is provided for all intensity steps for a number of energy [sic] over some minutes. The particle rate fed from the accelerator to the irradiation station lies between $2 \times 10^6$ and $2 \times 10^8$ ions per extraction from the synchrotron 5. The deviation of the particle rate from the desired preset value may be a maximum of 30% upward and a maximum of 50% downward. If these limiting values are exceeded, appropriate intervention is necessary. In order to test the consistency of the therapy system, this check can be carried out daily, for example.

In the case of the data supply to the accelerators, irradiation planning and raster scan programming, the same dependent relationships between the energy, intensity and focussing variation must be used as a basis. In order to ensure this, the data inputs compiled on the accelerator side after the last therapy programming must be compared with those which are used for the raster scan programming and irradiation planning. Any deviation between these data inputs is not permissible. To check consistency, this check should be carried out before each irradiation block.

During irradiation, the accelerator sections required for the therapy are interlocked against (external) interventions, in order to avoid intentional and unintentional maladjustments. At the same time, operating states of all the components are activated and access is made exclusively to the device reference data stored in memories, for example EPROMs. The function of this accelerator interlocking against interventions can be checked by a "supercycle" being created which contains both experimental and therapy accelerators. Monitoring means or detectors, such as profile gratings, luminous targets and ionization chambers (described in more detail below), are moved into the high energy beam guidance 6 to the rotating frame 8, and beam-influencing elements belonging to the high energy beam guidance line 6 and to the synchrotron 5 for the therapy accelerator are deactivated. The accelerator interlocking is then activated and all the experimental accelerators are deactivated while the therapy accelerator is activated. In addition, all the previously deactivated components for the therapy accelerator are activated and the profile gratings, luminous targets and ionization chambers moved in are moved out again. Then, individual magnets are sent shutdown commands, and beam guidance diagnostic components are sent actuating commands which, in the normal case, must not have any effects on the basis of the interlocking of the accelerator. Otherwise, there is a fault which must be corrected appropriately. For testing consistency, this check can be carried out before each irradiation block.

The extraction of the treatment beam from the synchrotron 5 must, for safety reasons, be able to be interrupted within less than 1 ms following a corresponding signal from an interlock unit belonging to the therapy system. This is done by rapidly shutting down a specific quadrupole in the synchrotron 5. The time between a request to break off the radiation, from the control and safety system, and the absence of the beam at the irradiation site is of critical importance both for the raster scanning procedure during the change between successive isoenergy sections, which correspond to areas to be irradiated at constant energy, and also for any emergency shutdown of the system in the event of a fault. A test is therefore provided which measures the total time, that is to say both the reaction time of the request and also that of breaking off the beam. For this purpose, the control system generates a corresponding signal which simulates the termination of an isoenergy section, or an interlock condition, that is to say a condition for an emergency shutdown, is generated. The control system then measures the number of particles after a shutdown, this having to be no greater than $10^4$ particles/s 1 ms after the shutdown. In addition, using a storage oscilloscope and a pulse generator, which are permanently installed in the technical control room of the therapy system, a measurement is carried out which evaluates the output signal from the current/voltage converter of one of the ionization chambers, in order in this way to check the above-described measurement of the control system. In the case of this second measurement, too, no beam must be capable of detection 1 ms after shutdown. The following times in a shutdown should be checked one after another: at the beginning of the extraction time, in the middle of the extraction time, at the end of the extraction time and outside the extraction time. As a consistency test, the check should be carried out daily.

After each irradiation has been concluded, a log must be drawn up on the accelerator side, which documents the settings of significant accelerator components during the irradiation and also selected beam diagnostic measurement results. In order to test the serviceability of the log and the content of the log, it is proposed to activate a reference therapy cycle and to call the logging program. Then, the logging data drawn up by the logging program can be compared with the expected data, an intervention having to be made in the event of incompleteness of the log or in the event of the presence of a logged device fault. To check consistency, this testing procedure can be carried out before each irradiation block.

A further section of the testing system relates to checking the guidance of the treatment beam (upstream of the treatment station).

From the accelerator outward, it must be ensured that in the event of a shutdown request, an extraction shutdown has been carried out. Should the treatment beam not be shut down by the shutdown request, this will be determined by the control and safety system by means of an intensity measurement, and a shutdown of the beam will be requested again via a redundant channel provided separately. This second request acts on a corresponding deflection dipole in the high energy beam guidance line 6. In order also to check the serviceability of this redundant extraction shutdown, the alarm line provided for the first extraction shutdown is interrupted artificially. In this case, the previously described second extraction shutdown would have to be triggered automatically, which can be tested in a similar way to the above-described check on the actual extraction shutdown. If an extraction shutdown does not occur within 10 ms, appropriate intervention is necessary. To test consistency, this test can be carried out before each irradiation block.

A further test can be used to test the function of connecting and disconnecting the dipoles arranged in the high energy beam guidance line 6. For reasons connected with patient safety, switching off the last two deflection magnets in the high energy beam guidance line 6 upstream of the irradiation (after the accelerator interlock) can be activated only from the technical control room via specific cable connections to the power supply unit of these magnets. As a result of this disconnection, the beam feed at the irradiation station is suppressed. The connection of these magnets can be carried out only from the technical control room via a specific signal and not (as usual) from the main control room of the accelerator. The function of this connection and disconnection is tested, the corresponding connections/terminals being checked at the same time. To test consistency, this test is carried out before each irradiation block.

A further section of the testing system relates to checking the beam guidance at the irradiation station.

According to a first aspect of this test section, the zero point position of the treatment beam is monitored. In order to ensure accurate beam positioning at the isocenter 10 after the beam 11 has been deflected by the raster scanner magnets 13, 14, the axial position of the treatment beam 11 in the last part of the beam guidance to the irradiation station must be checked for the entire energy and focussing range. For this purpose, profile gratings 16 are moved into the beam path downstream of the raster scanner magnets 13 and 14 and also at the beam exit window, and test cycles over the entire energy and focussing range are produced. In this case, the profile gratings are evaluated individually and the beam parameters recorded in the process are logged. During the measurement of the profile grating arranged at the beam exit window, the profile grating 16 previously arranged in front of said window must be moved out. By evaluating the beam parameters supplied by the profile gratings, the beam position and the beam angle can be determined both in the horizontal and in the vertical direction. From the beam positions of the profile gratings, the position to be expected of the treatment beam at the isocenter 10 is determined, and the log is then checked. If, for the isocenter 10, a positional error of ±25% with respect to the required beam half-width is determined in this process, an appropriate intervention must be made. To test consistency, this test can be carried out daily.

According to a further aspect of this testing section, the absolute beam location and the locational stability of the treatment beam at the irradiation station is checked. The maintenance of the absolute beam position is the precondition for the implementation of the treatment or irradiation plans. Therefore, the absolute location must be measured using location-sensitive detectors belonging to the control system. The relative locational stability of the treatment beam in the isocenter of the irradiation station determines the accuracy with which an irradiation plan can be carried out. The location of the treatment beam is measured and checked on line, that is to say continuously, during irradiation. In the event of deviations from the desired location within a tolerance limit predefined by the irradiation plan, the irradiation is broken off or an appropriate intervention is initiated. Each location-sensitive detector is checked separately.

The testing is carried out with a profile grating and location-sensitive detectors, such as multiwire chambers.

If profile gratings are used the absolute beam position at the isocenter 10 is checked with the aid of a luminous target or film at the location of the isocenter. Here, the position of the profile grating is adjusted by using an isocenter which is made visible by a laser cross on the luminous target or film. Using the raster scanner magnets 13, 14, the treatment beam 11 is deflected statically into the isocenter 10, and the location coordinates obtained by the profile grating measurement are compared with the predefined desired values. This can be carried out, for example, at regular intervals, for example during approximately every tenth energy step.

If multiwire chambers are used for the online monitoring and control of the beam position, two multiwire chambers are positioned at a distance of about 970 mm and 790 mm in front of the isocenter 10 and, with the aid of a laser beam, are aligned in such a way that the central beam running through the isocenter 10 runs at right angles through the center of the multiwire chambers. Using the raster scanner magnets 13, 14, the beam is deflected statically, for example at five different energies at five different positions in each case within the irradiation region (namely above and below in each case on the left and right and at the center). The location of the adjustment is measured by the control system and compared with the desired values.

Since the multiwire chambers are located at different distances in front of the isocenter, the irradiation field in the two multiwire chambers is imaged on a reduced scale with different factors. Applying the rules of beam geometry and the radiation law results in the following reduction factors:

Multiwire chamber 970 mm upstream of the isocenter:
x coordinate: reduction factor 0.890
y coordinate: reduction factor 0.876

Multiwire chamber 790 mm upstream of the isocenter:
x coordinate: reduction factor 0.910
y coordinate: reduction factor 0.899

Before checking the absolute beam position with the multiwire chambers, a calibration of their absolute positions should be carried out. For this purpose, after the multiwire chambers have been aligned and fixed, a film positioned absolutely by means of the laser cross mentioned previously is irradiated at five positions. The beam zero point determined by using the film is compared with that calculated from the multiwire chambers. The difference or deviation then gives correction offset values for the calculation of the location. These correction offset values are taken into account in the desired position values, the absolute position of all five points being compared with one another.

Using the multiwire chambers calibrated in this way, the absolute beam position is then checked, control being carried out in such a way that the positional deviation determined in this way corresponds at most to 25% of the half-width of the beam profile. This intervention threshold relative to the half-width of the beam profile has proven to be practicable, since all the geometric parameters of an irradiation plan are scaled with the half-width and, in particular, the quality necessary for the patient operation of the particle populations produced is achieved. When carrying out a consistency test, only the multiwire chamber measurements previously described should be used, since the installation of an additional profile grating in the isocenter would be very complicated for daily operation.

A further aspect of this testing section comprises the monitoring and control of the absolute beam profile width and the stability over time. The beam focussing supplied by the accelerator device as requested by a central pulse controller of the control system must be maintained, since the treatment or irradiation plans are based on these values. For this purpose, the absolute beam profile width at the isocenter 10 is checked with the aid of a profile grating, the position of the profile grating being adjusted with the isocenter made visible by a laser cross on a luminous target or film. Using the raster scanner magnets 13, 14, the treatment beam is deflected statically into the isocenter, it being possible for this to be carried out, for example, at about every tenth energy step. The beam widths obtained with the profile grating measurement are compared with predefined desired values, control being carried out in such a way that a maximum deviation of the beam width of ±50% of the preset defined value is maintained. This applies in particular for the energy range above 200 MeV/u.

Testing the consistency of the ion beam therapy system can again be carried out with the multiwire chambers already described previously, which are located at a distance of 970 mm and 790 mm, respectively, upstream of the isocenter 10. Before the actual test, calibration of the absolute width measurement of the two multiwire chambers is carried out. In this case, a film is irradiated with horizontal and vertical stripes, each beam being produced with an extraction from the synchrotron with fixed focussing. In this way, depending on the selectable focussing, seven beams can be produced, for example. The beam widths determined by using the irradiated film are compared with those measured by the multiwire chambers (location chambers), in order from them to obtain correction offset values which can subsequently again be taken into account in the desired values. Then, with the aid of the multiwire chambers calibrated in this way in conjunction with the control system, the half-width of the beam profile and its consistency or stability over time are measured and monitored, this being carried out in particular at different energies and intensities for the respectively selectable focussing.

Raising the intervention threshold from 20% to 50% of the half-width, as previously described, when measuring the absolute beam profile width as compared with measuring the absolute beam location is compatible with the homogeneity requirement, since the distance between the beam positions is set to 33% of the half-width within the context of the irradiation planning.

Upstream of the isocenter there are usually some elements for the analysis and modulation of the treatment beam, such as the beam exit window, detectors or a ripple filter. These elements bring about scattering of the treatment beam, which increases sharply with decreasing beam energy. As a result, for physical reasons, maintaining the originally required beam width in the lower energy range (energies less than 200 MeV/u) can no longer be realized, or realized only with difficulty. In this case, the result would be exceeding the upper tolerance values, so that this effect has to be taken into account in the irradiation planning.

A further aspect of this testing section relates to monitoring the number of particles in the treatment beam, that is to say monitoring the variation in the number of particles. In order not to permit the measurement range for particle number measurements to become excessively large, the intensity of the treatment beam supplied by the accelerator should fluctuate only within specific tolerance limits. In the present case, it is proposed to measure the intensity of the treatment beam with the aid of the ionization chambers in conjunction with the measurement apparatus of the monitoring system and to average the number of particles over a time window of 300 $\mu$s. The particle numbers subsequently measured within the time window must correspond at most to five times the value of the previously registered average in order not to trigger an intervention. As a result of these measures, a safe measurement range can be selected, with which it is still possible to correctly measure numbers of particles which, for example, are higher by a factor 10 than the previously calculated average. If still higher particle numbers should occur, an alarm will be triggered, and the interlock unit previously mentioned will trigger the beam shutdown. However, consideration must be given to the fact that this testing aspect relates only to the presetting of the detectors and does not have any direct influence on the energy dose or the like. Even in the event of a variation in the particle number which lies considerably above the previously defined intervention threshold, the homogeneity (described later) of the particle populations may be adequate as a critical quality criterion.

Finally, with regard to safe and stable beam guidance at the irradiation station, the desired positions of all the moving parts between the last deflection magnets of the high energy beam guidance line 6 and the rotary frame 8 should be checked regularly, since each object located in the beam guidance leads to impairment of the beam quality at the irradiation station. It is therefore necessary to ensure that no moving parts belonging to the beam guidance are located in the beam path. For this purpose, limit switches are fitted to the corresponding moving parts, it being possible for their states to be checked automatically and individually by the monitoring system. This should be repeated before each irradiation block in order to test the consistency.

A further section of the testing system relates to checking the serviceability of the interlock unit of the ion beam therapy system, already described previously.

For example, all the safety-relevant device parameters must be checked for the triggering of an emergency shutdown of the system in the event of an interlock case or an interlock condition. The treatment beam 11 can be shut down only if an interlock case is detected. Therefore, all sources which can lead to an interlock case must be simulated individually in a test, and the triggering of the interlock, that is to say the generation of the signals leading to the emergency shutdown of the treatment beam 11 by the interlock unit, must be checked. During operation, the interlock unit monitors, for example, the signals from the above-described limit switches of the moving parts in the beam guidance, the states of the magnetic network devices of the raster scanner magnets 13 and 14, checks the ionization chambers with regard to the voltage supply, a data overflow in the data transmission, compliance with the intensity limiting values and the synchronism of the individual ionization chambers, the electronics of the beam position measuring device and the beam position itself, the high voltage and the gas flow of the individual detectors, a possible interlock coming from the sequence control computer, the position of the patient couch, a possible interruption to the immobilization of the patient (for example when opening the mask at the irradiation station or in the event of a movement of the patient), the functional readiness of all the computer programs and a possible emergency shutdown or release of irradiation by means of the medical operating console of the therapy system etc. If the interlock does not trigger when an interlock state is present, action must be taken in the therapy system and the fault must be rectified. In order to test consistency, this check should be carried out daily.

Likewise, the serviceability of the manual emergency shutdown via the medical operating console must be checked, since manual emergency shutdown must be ensured at any time.

Finally, a check on the displays of all the safety-relevant states on the individual consoles of the ion beam therapy system, in particular of the technical control rooms and the main control room, is needed. The display of these safety-relevant states is used for rapid fault detection and fault rectification, and provide [sic] the operating personnel with information about the instantaneous state of the irradiation. These displays of the alarm conditions can be checked together with the above-described test of the interlock unit. In order to test consistency, this test should be carried out before each irradiation block and after any change to the monitoring system or to the programs.

A further section of the testing system relates to checking the medical equipment for patient positioning of the ion beam therapy system.

For example, the accuracy of the stereotactic coordinate determination of a target should be checked with the aid of a CT or MR method, since the accuracy of the stereotactic imaging is a significant factor for the overall accuracy of the irradiation. For this purpose, any desired target within a spherical phantom can be represented by a special test body whose center can be represented in an easily visible manner with the aid of the imaging methods. The spherical phantom is clamped into the stereotactic frame, so that the center becomes an unknown target. The stereotactic coordinates are then determined successively with the aid of the radiographic, CT or MR methods used; in the case of the tomographic methods, the layer spacing should be 1 mm.

Since the accuracy of the radiographic method is accurate to $\frac{1}{10}$ mm, the accuracy of determining the target with CT and MR can be determined by comparison with the radiographic method, that is to say the radial distance between the position of the target determined with the radiograph and the position determined with the CT or MR method is checked. The radial distance must not be more than 1.5 mm. To test consistency, it is sufficient to carry out this test annually.

As a further testing aspect, it is proposed to check the accuracy of the position of the isocenter between the axis of rotation of the patient couch 9 and the central beam 11 from the raster scanner 13, 14, since the isocenter, defined as the point of intersection between the axis of rotation of the patient couch 9 and the central beam 11 from the raster scanner 13, 14, is the connecting element in the positioning between planning and irradiation. A consistency test should be carried out before each irradiation block.

In order to check the isocenter in relation to the axis of rotation of the patient couch 9, a metallic test body (2–3 mm diameter) is moved, with the aid of lasers, into the nominal isocenter, that is to say into the nominal axis of rotation of the patient couch 9. The position of the test body is determined by means of a plumb line, which is aimed accurately at the center point above the test body. During rotation about the axis of rotation of the patient couch 9, the extent of the movement of the test body in relation to the plumb line is determined. This procedure is carried out at at least three different heights of the patient couch 9; in the event of a maximum adjustability of the patient couch 9 of 15 cm upward/downward, for example, at the height of the isocenter 10 and with at least 15 cm spacing upward and downward. The maximum deviation may be 1.0 mm in the beam direction and only 0.5 mm at right angles to the beam direction. Changes in the beam direction are less critical, since dose distributions in the patient are not influenced by these.

In order to check the isocenter in relation to the central beam 11, the position of the isocenter is defined by definition on the axis of rotation of the patient couch 9 underneath the straight-ahead beam plane, and is defined by an optical measuring system in relation to wall markings. Testing the position of the test body in relation to the central beam 11 is carried out with the aid of a film measurement, a verification film downstream of the sample body (as viewed in the beam direction) being irradiated with an (unscanned) central beam, its half-width being greater than the diameter of the test body, so that the position of the test body in relation to the central beam is imaged on the verification film. In this case, the intervention threshold is located at a deviation of at most 25% of the half-width of the primary beam.

In addition, the accuracy of the laser adjustment onto the isocenter 10 must be checked, since the lasers mark the isocenter 10. In this case, after the test body has been positioned in the isocenter 10 with the aid of optical measurement, the lasers are aligned with the center of the test body and the deviation of the laser lines from their horizontal and vertical is checked; the maximum deviation in each case may be 1 mm. To test consistency, the image of the laser is marked on the opposite walls or on the floor and is subsequently used as a reference value.

A further testing aspect relates to the accuracy of adjustment of the X-ray tubes and the target cross on the opposite recording stations, since the radiographic method represents an additional method of marking the isocenter 10. Following the positioning of the test body in the isocenter 10 with the aid of optical measurement, that is to say with the aid of the lasers, radiographs are made in the three spatial directions and the distance of the image between the test body and the target cross is determined on the radiograph. The test body should be imaged exactly on the image of the target cross, so that the maximum distance between the image of the test body and the target cross may be 1 mm.

Because of the isocentric irradiation of the patients, the accuracy of the display of the angle scale of the isocentric rotation of the patient couch 9 must also be checked, it being possible for this to be carried out in analogy with the stipulations of DIN 6847-5, point 12.2.4. The maximum tolerable inaccuracy is 1°.

Likewise, the spatial stability of the isocentric rotation of the patient couch 9 should be checked, since the definition of the isocenter 10 assumes a corresponding stability. This check can be carried out in analogy with DIN 6847-4, point 14.2, the intervention threshold being at an inaccuracy of 1 mm.

Finally, it is also proposed to check the accuracy of the patient support and positioning, since exact patient positioning is a precondition for tumor-conformal irradiation. For the purpose of acceptance testing and consistency testing (before each irradiation block) of the therapy system, in this regard the unknown stereotactic coordinates of the center of a test body, which has been fixed within the stereotactic base ring, is determined as the target, and the center is brought into the isocenter 10 with the aid of the stereotactic aiming device and by means of transversal movement of the patient couch 9. In this position, radiographs are made in the three spatial directions and the distance between the position of the test body and the target cross is determined on the three radiographs. The radial distance between the center of the test body and the isocenter may be a maximum of 1.5 mm. Otherwise, appropriate correction of the patient support is necessary.

A further section of the testing system relates to irradiation planning, in the course of which, in particular, the irradiation dose values intended for a specific irradiation are calculated.

First of all, it must be ensured that the same basic data sets are always used for the planning of irradiations, that is to say for the calculation of each irradiation dose. This can be done by the name, the date and the size of the files containing the basic data being compared with the correct designations of a previously created security copy. This is carried out automatically each time the dose calculation algorithm is called.

In addition, the identity of the values from the current basis data sets with the corresponding values from a security copy must be checked, in order to ensure that the basic data sets have not been changed without being inspected. Here, too, the comparison between the content of the current basic data sets and the security copy is carried out with the aid of a computer program which, in particular, should be started before each irradiation block.

According to DIN 6873 Part 5, irradiation planning systems, testing the reference values in the basic data set is additionally required once per month. This secondary point can be dispensed with in the case of the present irradiation planning with heavy ions, since the depth dose distributions, that is to say the energy loss data as a function of the depth, are stored as absolute values with reference to the input fluence. For this reason, no special reference value for the dose is recorded. The basic data sets used have already been checked as described above.

A significant aspect when testing the irradiation planning is checking the accuracy of the dose calculation carried out automatically in the ion beam therapy system for a planned irradiation on the basis of the existing basic data and the dose calculation algorithms used, a distinction having to be drawn here between the irradiation of a homogeneous and of an inhomogeneous medium. In both cases, checking the dose calculation can be carried out by using a phantom, which will be described in more detail below.

In order to check the calculated dose for a homogeneous medium, a number of measurement points, for example 10 measurement points, can be defined in the irradiation planning program of the ion beam therapy system, at which points calculated dose distributions or CT sections are defined at which the calculated physical dose is to be verified experimentally. The verification is carried out in a water phantom, ionization chambers being positioned in the water phantom at the coordinates corresponding to the desired measurement points. For the individual measurement points, the irradiation planning program, in addition to calculating the water energy dose values, also calculates their coordinates in the phantom used. The phantom is then irradiated with the control parameters calculated by the irradiation planning program, the values registered by the ionization chambers being converted into energy dose values in order to verify the calculated dose values.

The verification is carried out for a plurality of irradiation plans, six typical irradiation plans preferably being verified, of which three plans relate to constructed target volumes in the water phantom and three plans relate to the irradiation of patients. The last-named irradiation plans are then used as standard patient plans. The values calculated by the irradiation calculation program are used as reference values for the consistency testing to be carried out.

As an intervention threshold, it is defined that the deviation between the calculated and the measured irradiation dose values overall, that is to say on average, may be at most ±5% of the dose of the target irradiation volume. In addition, it is defined that the maximum deviation for an individual measurement point may be ±7%.

The procedure described above relates in particular to the acceptance testing of the ion beam therapy system. For consistency testing, the verification of only two of the standard plans described above is sufficient in each case to check the consistency of the calculated dose distributions and to compare these with the dose distributions to be determined experimentally. The consistency testing should be carried out before each irradiation block.

To check the accuracy of the dose calculations as a function of the basic data, the irradiation calculation algorithms used and the approximation used for an inhomogeneous medium, a spherical solid body phantom can be used which consists of a water-equivalent material and is constructed from individual layers, into which different inhomogeneities can be inserted for the purpose of simulating various inhomogeneous bodies. These inhomogeneities are disks which consist of various tissue-equivalent materials (for example corresponding to the material of the lung, a soft or hard bone, soft parts or bound water) or only air (when a disk is not inserted). In this case, too, up to 10 measurement points in the phantom are defined for verification, at which in each case the irradiation dose is both calculated by the irradiation planning program and also registered with a set of ionization chambers which measure simultaneously, and is therefore compared.

For the purpose of acceptance testing, it is proposed to carry out three different phantom constructions to investigate the calculated dose distribution behind boundary layers of different materials (for example air/water and bone/water), in thin inhomogeneities and in thick inhomogeneities.

In addition, when investigating the calculated dose values for inhomogeneous media, it is proposed, as a tolerance threshold, to permit a maximum average deviation between the calculated dose values and the measured dose values of all measurement points of ±5%, and a maximum deviation for an individual measurement point of ±7%. For consistency testing, the previously described tests can be carried out before each irradiation block.

Likewise, the dose calculations can be verified by using an irregularly shaped test phantom. In this case, a test phantom is used which consists of water-equivalent material and, for example, simulates a human head. As previously described, up to 10 measurement points are defined in the phantom for verification. In addition, irradiation parameters for a suitable target irradiation volume in the head phantom are defined, and the test phantom is adjusted with the aid of the stereotactic base ring. Then, the values of the water energy dose calculated by the irradiation planning program of the ion therapy system at the selected measurement locations is compared with the values measured by the ionization chambers at these measurement points; again, the deviation for all the measurement points may be a maximum of ±5% of the dose of the target irradiation volume, while for each individual measurement point, a maximum deviation of ±7% is permissible. To test consistency, this test can be carried out before each irradiation block.

A further aspect in the checking of the irradiation planning relates to testing the imaging methods used in the ion beam therapy system, in order to ensure the correct transmission of the geometric structures (for example of the target irradiation volume and of the contours of the patient) and also of the planning parameters from the imaging as far as the positioning. For this purpose, as in the case of the verification of the calculated irradiation dose values in the inhomogeneous medium, a phantom with disklike or annular inserts can be used, it being possible in this case for the inhomogeneous inserts additionally to have different diameters. An image of the phantom is recorded, and digital radiographic reconstructions for the three main directions in the rotating frame 8 (cf. FIG. 2) are calculated from the CT data obtained in this way. Verification of the planning geometry is then carried out with the aid of radiographs from the X-ray positioning system in the three main directions. This procedure can be carried out at various angles of the patient couch 9 shown in FIG. 2, for example at 0°, 45° and 90°. In this way, the shape and the position of the inhomogeneities in the digital radiographic reconstruction are verified with reference to the radiographs of the X-ray positioning system. The tolerance thresholds defined in this case are that both the maximum positional deviation and the maximum deviation with regard to the shape of the rings of the phantom may be 2 mm. The consistency testing can again be carried out before each irradiation block.

In order to increase the operational safety, in addition monitoring the maintenance and further development of the irradiation planning programs used in the ion beam therapy system is required. Following any development of the irradiation planning programs, a wrong version can inadvertently be used. In order to avoid this and to ensure that the correct versions of the different modules are always used, the monitoring system of the ion beam therapy system is configured in such a way that each time an irradiation planning program is called, version numbers with the date of the respective program are displayed, and must be compared by the user with data in a log book.

It is likewise necessary to ensure that, in the event of development of the irradiation planning program, that is to say when a new version is present, this is put into effect only after renewed acceptance testing. This can be carried out by complete dose distributions being calculated as described above for a homogeneous medium, an inhomogeneous medium and for an irregularly shaped phantom and saved as a security copy. When the new program version is used, these stored dose values can be used as reference values for verifying the serviceability of the new program version since when the new program version is used for the same phantom, the same dose values would have to be calculated. This check should therefore be carried out after any change to an irradiation planning program.

A further section of the testing system relates to checking the raster scanning process and the dosimetry.

In this case, a first testing aspect of this testing section relates to particle-number monitoring means belonging to the ion beam therapy system which in the case of the present exemplary embodiment—as has already been described—comprise large-area ionization chambers.

In this regard, for example, the consistency of the calibration factors of these ionization chambers must be checked, since the calibration factors may change only within the context of air density fluctuations. The two ionization chambers of the raster scanner are calibrated with regard to the number of particles per monitoring unit of the ionization chambers. The calibration is described by a calibration factor K, which depends on the irradiation energy E of the particles and the step width $\Delta x$ and $\Delta y$ of the raster scanner, that is to say $K=K(E, \Delta x, \Delta y)$. The calibration of the ionization chambers is carried out via a dose measurement in a homogeneously scanned irradiation field, the deviations from the reference conditions being corrected and the display from the ionization chambers being converted into a water energy dose $D_{scan}$. The calibration factor is calculated in accordance with:

$$K(E, \Delta x, \Delta y)=(D_{scan}/M_i)\cdot \Delta x\cdot \Delta y/(S(E)/\rho)$$

where $(S(E)/\rho)$=mass stopping power of $^{12}C$ at an irradiation energy E, and M=monitor units per coordinate point i of the ionization chamber.

The relevant energy range (for example between 80 MeV/u and 430 MeV/u) is measured in a number of steps. The measurement location of the respectively checked ionization chamber is located at the isocenter 10, the ionization chamber or the dosimeter being arranged in a solid body phantom. The same table of the mass stopping power of $^{12}C$ on which the irradiation planning was also based is used. In this way, depending on the energy E and the step width $\Delta x$, $\Delta y$, a set of calibration factors K is obtained, it being defined that the deviation from the reference values may be a maximum of ±3% for each calibration factor. From the set of calibration factors, at least three values should be checked. To test consistency, this testing method should be carried out daily.

The dose consistency must also be checked, since identical preselected monitor units of the ionization chambers must always lead to identical dose displays. It is therefore recommended to check the consistency of the dose at the center of cube-shaped irradiation volumes, which are produced or scanned by the raster scanner or its magnets 13, 14, as a function of the set of calibration factors of the ionization chambers. For this purpose, in order to obtain reference values, the dose is measured in a phantom which is positioned in such a way that the isocenter 10 is located precisely at the center of its front surface. In this case, the irradiation is carried out within an irradiation or dose cube with 5 cm edge length, whose center, as measurement location, is arranged at an 11.3 cm water-equivalent depth. (The calculation of the control data for producing the dose cube is carried out with the aid of CT-based irradiation planning. For this step, it is more expedient to place the isocenter 10 at the location at which the beam enters the water phantom. In addition, the selected measurement depth permits standardization of the measurement equipment for the different tests.) The irradiation dose determined in this way is stored as a reference dose. The actual dose values subsequently measured can then be compared with this reference dose, a maximum deviation between the actual and the nominal dose (reference dose) of ±3% being permissible. In this case, a daily consistency test should be carried out.

In addition, the parameters influencing the particle number monitors or ionization chambers must be checked, in particular the dependence of the calibration factors K on the particle fluence and the particle flux being checked. In both cases, an annual consistency test should be carried out.

In order to check the dependence of the calibration factors on the particle fluence, substantially the same method as in checking the consistency of the calibration factors is carried out. The measurements are carried out in a phantom which, with an area of 5×5 cm$^2$, is irradiated with the same beam intensity in each case at the energy levels 150 MeV/u, 250 MeV/u and 350 MeV/u. An ionization chamber is arranged in the center of the irradiated area. The monitor values from the ionization chamber are defined in such a way that a dose of 0.2 Gy, 0.5 Gy and 1 Gy results at the measurement location in each case. For these different monitor values, the agreement between the actual and the nominal dose is registered, a maximum deviation of ±3% being permissible. Complying with this close tolerance is expedient and also feasible.

In order to check the dependence of the calibration factors on the particle flux, likewise substantially the same method as in the checking of the consistency of the calibration factors is applied. In this case, however, the dose is kept constant and the beam intensity is in each case set to a high, medium and low value, so that the agreement between the actual irradiation dose and the nominal reference dose can be checked for different intensities. Here too, a maximum deviation of ±3% is permissible.

With regard to the ionization chambers or particle-number monitors, the dependence of their calibration factors on the beam position should also be checked. Substantially the same method as in the checking of the consistency of the calibration factors is carried out, but the same arrangement as in the case of the previously described checking of the dose consistency is used. The measurements are carried out in an irradiation volume or irradiation cube of the raster scanner 13, 14 with an edge length of 5 cm, but with a lateral offset of 2 cm and 6 cm. In this case, the monitor values of the ionization chambers are defined in such a way that the result is an irradiation dose of 1 Gy at the center of the irradiation volume. When checking the displays of the ionization chambers, the value measured at the side should not differ by more than 3% from the value measured at the center. In this case also, a yearly consistency test is recommended.

A further testing aspect of this testing section relates to checking the dose distribution of the raster scanner 13, 14, both the depth dose distribution and the transverse dose distribution being checked.

The homogeneity of the depth dose distribution is checked as a function of a selected irradiation energy and selected monitor values per irradiation energy value of the ionization chambers used, since the depth dose homogeneity depends critically on the energy selected and its consistency. For this purpose, the raster scanner magnets 13, 14 are again used to generate box-like or cube-like irradiation volumes in a phantom, a constant particle population being used for each coordinate point in a layer (energy), but a different particle population for each layer, such that the result is a homogeneous dose distribution in the irradiation cube. A number of dosimeters (ionization chambers), for example 10 ionization chambers, measure at different water-equivalent depths, the ionization chambers being positioned in such a way that a plurality of ionization chambers are not irradiated one behind another. The edge lengths of the irradiation cubes are, for example, 2.5 cm, 5 cm and 10 cm, the measurements of the ionization chambers being carried out for depths of the centers of the respective cube-like irradiation volumes of 5 cm, 12.5 cm and 20 cm, respectively. The monitor values are defined from the irradiation planning in such a way that a radiation dose predefined by the irradiation planning results at the center of the respective irradiation volume. By comparing the actual measured values with the reference values, the range of fluctuation of the displays of the ionization chambers can be checked. A maximum deviation of ±5% is tolerable. If this tolerance limit is exceeded, intervention must be made in the system in order to correct the excessively high deviation. For consistency testing, the above-described testing method should be carried out before each irradiation block.

The transverse dose distribution of the raster scanner is checked as a function of the energy, in order to ensure that the homogeneity of the raster scanning method is ensured at all the irradiation energies used. In this case, with fixed ionization chamber monitor values and respectively different irradiation energies (e.g. 100 MeV/u, 150 MeV/u, 200 MeV/u, 250 MeV/u, 300 MeV/u and 350 MeV/u) and beam fields, the irradiation dose at right angles to the beam direction is defined with a number of ionization chambers measuring simultaneously. At the same time, with free air in front of the dosimeters or ionization chambers, a blackening distribution on a verification film is produced. Using the raster scanner 13, 14, areas with a side area [sic] of, for example, 5 cm, 10 cm and 18 cm are produced, the intention being for the irradiation dose to be about 1 Gy in each case. The standard deviation of the corrected displays of the ionization chambers and the verification film blackening within the irradiation field is checked, a maximum deviation from the reference values of ±5% being tolerable. Non-tolerable deviations from the reference values are corrected, in order to achieve matching to the measurement conditions actually present. A consistency test should be carried out before each irradiation block, in this case the use of the verification film with monitoring of the blackening of this verification film being sufficient.

A further testing aspect of this testing section relates to checking the field geometry in the raster scanning method, the dependence of the spatial position of a specific irradiation volume of the raster scanner 13, 14 of selected irradiation energies being checked. For this purpose, cube-like or box-like irradiation volumes are generated by the raster scanner 13, 14, a constant particle population being used for each coordinate point of a layer (energy), but a different population for each layer, in such a way that the result is a homogeneous dose distribution in the irradiation cube. Under these conditions, a wedge-like solid body phantom is irradiated, behind which there is a verification film. The position of the verification film blackening relative to the center of the irradiation is subsequently determined.

During the measurement, the edge lengths of the irradiation fields are, for example, 4 cm, 7 cm and 12 cm, while the extent of the irradiation boxes or cubes in the beam direction is 2.5 cm, 5 cm and 10 cm. The measurements are carried out for water-equivalent depths of the center of the respective irradiation volumes of 5 cm, 12.5 cm and 20 cm, respectively. The monitor values of the dosimeters or ionization chambers are defined from the irradiation planning in such a way that, at the center of the irradiation volume, the result is an irradiation dose predefined by the irradiation planning. The field limits defined are the locations at which the edge drop of the blackening is at 50% of the plateau value. The position of the distal field limits and the lateral field limits, as viewed in the beam direction, are checked and compared with reference values. A deviation of 2 mm in each direction is tolerable, otherwise a correction must be made to the system in order to adapt the system to the measurement conditions actually present. This testing method should be carried out before each irradiation block in order to test consistency, here a selection of three conditions in each case from the combinations of the previously described conditions being sufficient.

Finally, a further testing aspect of this testing section relates to the verification of the overall system, in order to be able to verify the accuracy of the applied irradiation dose with regard to its level and spatial extent in each patient to be irradiated, so that the correct cooperation between the individual components of the system is ensured. In this case, a distinction is drawn between the irradiation of a homogenous medium and of an inhomogeneous medium.

In the first case, as in the previously described verification of the agreement between calculated and measured dose distributions for a homogeneous medium, a homogeneous phantom is used and substantially the same method is carried out, but with the exception that individual patient irradiation plans are now used as a basis. For all the measurement points, the difference between the calculated irradiation dose and the measured irradiation dose is determined, an average deviation for all the measurement points of 5% and a deviation for an individual measurement point of 7% again being tolerable. To test consistency, this test should be carried out before each irradiation block.

In order to check the accuracy when irradiating an inhomogeneous medium to be irradiated, again an inhomogeneous phantom is used, in this case, as a one-off preparation, irradiation planning being carried out for a hemispherical phantom consisting of a solid, water-equivalent material with a radius of, for example, 8 cm. For the irradiation planning, the center of the phantom is at the isocenter 10 and the hemisphere of the phantom faces the incoming beam direction. Different inhomogeneities, for example in the form of disks with a diameter of 3 cm in each case, can be inserted into the phantom, use preferably being made of seven different materials or inhomogeneities with the following densities:

| No. | Density | |
|---|---|---|
| 1 | 0.001 | (Air) |
| 2 | 0.30 | (Lung) |
| 3 | 1.035 | (Bound water) |
| 4 | 0.92 | (Fat) |
| 5 | 1.05 | (Muscle) |
| 6 | 1.14 | (Soft bone) |
| 7 | 1.84 | (Hard bone) |

The planned target irradiation volume, for three different incoming beam directions with an input beam angle of 0°, +45° and −45°, is in each case a layer 2 cm thick within the hemispherical phantom, said area adjoining the flat side of the hemisphere directly, so that the distal position of the irradiation volume coincides with the rear flat side. The planned homogeneous irradiation dose in the target irradiation volume is 1 Gy. Using these control data for controlling the raster scanner, the irradiations are carried out with the three incoming beam directions, a dosimeter (that is to say an ionization chamber) being positioned both in the target irradiation volume and also behind each inhomogeneity, and its display being monitored. The determined energy dose at all the measurement points should not exceed the threshold 1 Gy±5% within the target irradiation volume, while 5 cm behind the target irradiation volume a maximum deviation of ±10% from the irradiation dose calculated and based on the target irradiation volume is tolerable. In addition, for all the measurement points, an average deviation of the measured irradiation dose of ±5% is tolerable, and, for each individual measurement point, a maximum deviation of ±7%. In order to test consistency, this testing method should be carried out before each irradiation block.

What is claimed is:

1. A method of checking the irradiation control unit of a heavy ion beam therapy system, the heavy ion beam therapy system comprising at least one ion source (1), an accelerator device (2, 5) for accelerating the ions from the ion source (1) in the form of a treatment beam (11), a beam guidance system (6, 8) in order to feed the treatment beam (11) from the accelerator device (2, 5) to at least one irradiation station for treating a patient, the beam guidance system (6, 8) comprising at least one beam guidance line (6), and a raster scanning device arranged in the beam guidance system (6, 8) and having vertical deflection means (13) and horizontal deflection means (14) for the vertical and horizontal deflection of the treatment beam (11) at right angles to its beam direction, so that the treatment beam (11) is deflected by the raster scanning device onto an isocenter (10) of the irradiation station and scans a specific area surrounding the isocenter (10), and data sets and permanently stored data of a control computer, parameters of measuring sensors, desired current values of scanner magnets, and and [sic] desired currents of scanner magnet currents being compared with actual magnet current values, characterized in that the permanent storage of permanently stored data is checked and calibration tests of measuring sensors are carried out, and in that the data sets and programs to be loaded into front end processors from the central control computer are read back after being loaded and are compared with the output data, all the data paths through which the data pass as they are loaded being checked when the data are read back, and specific programs writing the programs and data sets in server computers of a monitoring system into front end memories and reading said data back and comparing them automatically with programs and data in the dedicated memory before each irradiation and, only after it has been ensured by checking that all the programs and data sets which have to be loaded into front end computers of a monitoring system and executed from there correspond exactly to those on data memories of the monitoring system, safe operation being assumed.

2. The method as claimed in claim 1, characterized in that all the input data which are required for a patient irradiation are loaded into the sequence control of the central control computer.

3. The method as claimed in claim 1, characterized in that an alarm message is displayed by a therapy operating computer if deviations occur between data read back and output data.

4. The method as claimed in claim 3, characterized in that the central control computer and a monitoring computer are informed about the alarm.

5. The method as claimed in claim 3, characterized in that in the event of an alarm, an interlock unit is not released by the therapy operating computer, nor is a patient operation released.

6. The method as claimed in claim 1, characterized in that each deviation between the data read back and an original data set triggers an alarm.

7. The method as claimed in claim 1, characterized in that a last irradiation point in the event of a power failure is available as permanently stored data.

8. The method as claimed in claim 7, characterized in that the number of the irradiation point when a shutdown condition occurs is saved and stored as permanently stored data, in spite of power failure.

9. The method as claimed in claim 1, characterized in that in order to check the permanent storage of data, a monitoring system of the central control computer is loaded with an irradiation plan, this plan is carried out without an active beam, artificial switching from one irradiation site to the next is carried out, the voltage supply of a motherboard for processor cards is switched off at a well-defined treatment site and after the system has been restarted, the last irradiation site is read out and compared with the well-defined irradiation site.

10. The method as claimed in claim 1, characterized in that the checking of the permanent storage is carried out before each treatment block.

11. The method as claimed in claim 7, characterized in that in the event of deviations between the values read after the power failure and the values last present before the power failure, the therapy system is not released for patient treatment.

12. The method as claimed in claim 1, characterized in that the desired current values of scanner magnet currents are compared with the actual values in terms of value and time, the actual values being permitted to exceed neither value nor time tolerance limits.

13. The method as claimed in claim 12, characterized in that the maximum setting time for a current step of 2 A is checked for $dt_x \leq 175$ $\mu s$ and for $dt_y \leq 325$ $\mu s$.

14. The method as claimed in claim 12, characterized in that an absolute current accuracy of dI=0.3 A is required.

15. The method as claimed in claim 1, characterized in that a calibration check and monitoring of the temperature and pressure of the counting gas of an ionization chamber is carried out.

16. The method as claimed in claim 1, characterized in that pressure and temperature of the counting gas are measured with electronic sensors.

17. The method as claimed in claim 16, characterized in that the measured values are registered by a monitoring system and converted into absolute units with calibration factors input there.

18. The method as claimed in claim 16, characterized in that the calibration of the sensors is carried out with the aid of reference measuring instruments.

19. The method as claimed in claim 16, characterized in that the counting gas pressure and the temperature are registered and logged digitally.

20. The method as claimed in claim 16, characterized in that the external air pressure and the room temperature at the location of the monitoring system are measured with absolutely calibrated instruments.

21. The method as claimed in claim 16, characterized in that the absolute values for air pressure and room temperature are measured daily directly on the reference instruments, compared with the values displayed by the monitoring system and logged.

22. The method as claimed in claim 16, characterized in that the values for counting gas pressure and counting gas temperature are registered once per minute, and a time profile of the values is displayed graphically.

23. The method as claimed in claim 16, characterized in that an alarm is output if deviations of more than 20 hPA/5C (sic) are determined in the course of one day.

* * * * *